(12) United States Patent
Tromp

(10) Patent No.: US 8,586,919 B1
(45) Date of Patent: Nov. 19, 2013

(54) LOW-VOLTAGE TRANSMISSION ELECTRON MICROSCOPY

(75) Inventor: Rudolf Tromp, North Salem, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/535,980

(22) Filed: Jun. 28, 2012

Related U.S. Application Data

(63) Continuation of application No. 13/528,990, filed on Jun. 21, 2012.

(51) Int. Cl.
*G01N 23/00* (2006.01)
*G21K 7/00* (2006.01)

(52) U.S. Cl.
USPC ............ 250/307; 250/310; 250/311; 250/305

(58) Field of Classification Search
USPC ...... 250/305–307, 310, 311, 396 ML, 396 R, 250/397, 492.3
See application file for complete search history.

(56) References Cited

U.S. PATENT DOCUMENTS

| | | | |
|---|---|---|---|
| 4,415,851 A * | 11/1983 | Langner et al. ............... | 324/501 |
| 4,618,767 A * | 10/1986 | Smith et al. .................... | 250/311 |
| 5,767,516 A | 6/1998 | Kawanami et al. | |
| 5,789,748 A * | 8/1998 | Liu et al. ........................ | 250/310 |
| 6,610,980 B2 * | 8/2003 | Veneklasen et al. ............ | 850/8 |
| 6,759,654 B1 * | 7/2004 | Mankos et al. .................. | 850/9 |
| 6,803,571 B1 * | 10/2004 | Mankos et al. .................. | 850/9 |
| 6,803,572 B2 * | 10/2004 | Veneklasen et al. ............ | 850/9 |
| 6,878,937 B1 * | 4/2005 | Mankos ........................... | 850/9 |
| 6,943,360 B1 | 9/2005 | Mankos | |
| 7,217,924 B1 * | 5/2007 | Mankos et al. ............... | 250/310 |
| 7,348,566 B2 * | 3/2008 | Tromp ....................... | 250/396 R |
| 8,258,474 B1 * | 9/2012 | Mankos ........................ | 250/310 |
| 8,274,063 B2 * | 9/2012 | Kaito et al. ............... | 250/492.21 |
| 2002/0070340 A1 * | 6/2002 | Veneklasen et al. ........... | 250/310 |
| 2004/0000642 A1 * | 1/2004 | Veneklasen et al. ........... | 250/311 |
| 2004/0200960 A1 * | 10/2004 | Mankos et al. ............... | 250/310 |
| 2009/0321634 A1 * | 12/2009 | Khursheed ..................... | 250/307 |
| 2010/0288924 A1 * | 11/2010 | Kaito et al. .................... | 250/307 |

OTHER PUBLICATIONS

A. Delong et al., "Low voltage electron microscope I. Design," Proc. EUREM 12, 2000, pp. 197-198.
U. Kaiser et al., "Transmission electron microscopy at 20 kV for imaging and spectroscopy," Ultramicroscopy, vol. 111, No. 8, Jul. 2011, pp. 1239-1246.
H. H. Rose, "Future trends in aberration-corrected electron microscopy," Phil. Trans. R. Soc. A, vol. 367, 2009, pp. 3809-3823.

(Continued)

*Primary Examiner* — Bernard E Souw
(74) *Attorney, Agent, or Firm* — Cantor Colburn LLP; Vazken Alexanian

(57) ABSTRACT

Embodiments of the invention relate to electron microscopy. Example embodiments relate to an apparatus including a first electron beam source, a second electron beam source, and a receiving unit. The first electron beam source is configured to provide a first low-voltage electron beam to a surface of a sample. The second electron beam source is configured to provide a second low-voltage electron beam to pass through the sample. The receiving unit is configured to analyze the first low-voltage electron beam, or the second low-voltage electron beam, or both the first and the second electron beam to obtain information about the sample.

18 Claims, 6 Drawing Sheets

(56) References Cited

OTHER PUBLICATIONS

T. Schmidt et al., "Double aberration correction in a low-energy electron microscope," Ultramicroscopy, vol. 110, 2010, pp. 1358-1361.

S. M. Schramm et al., "Low-energy electron microscopy and spectroscopy with ESCHER: Status and prospects," IBM Journal of Research and Development, vol. 55, No. 4, Jul.-Aug. 2011, pp. 1:1-1:7.

Ilona Mullerova, et al "A Method of Imaging Ultrathin Foils with Very Low Energy Electrons," Ultramicroscopy, Elsevier, pp. 1-4; 2012.

* cited by examiner

LOW-VOLTAGE TRANSMISSION ELECTRON MICROSCOPY

CROSS REFERENCE TO RELATED APPLICATION

This application is a continuation of U.S. patent application Ser. No. 13/528,990, filed Jun. 21, 2012, the disclosure of which is incorporated by reference herein in its entirety.

BACKGROUND

The present invention relates generally to transmission electron microscopy, and more specifically, to transmission electron microscopy analyzing a sample using two low-voltage electron beams.

Electron microscopy provides an electron beam to a sample to analyze characteristics of the sample. Relatively high-energy electrons, such as between 10-20 keV may be emitted from an electron gun. The electrons travel through a condenser and an objective lens and are slowed by a sample bias or potential. At the surface of the sample, the electrons may have a low energy level, such as between near 0 eV-100 eV, and may interact with the surface of the sample and in a region within the sample that is close to the surface. The electrons backscatter and re-accelerate to the relatively high-energy level. The electrons may be projected onto an imaging plane, and patterns generated by the electrons may provide information regarding the sample, and in particular regarding a surface region of the sample.

SUMMARY

Exemplary embodiments include a first electron beam source configured to provide a first electron beam to a surface region of a sample, a second electron beam source configured to provide a second electron beam to pass through the sample, the second electron beam having an initial energy level less than an initial energy level of the first electron beam, and a receiving unit configured to analyze the first electron beam and the second electron beam to obtain information about the sample.

Additional exemplary embodiments include a system including an electron microscopy assembly and an imaging unit. The electron microscopy assembly is configured to provide a first electron beam to a surface of a sample without passing through the sample and to pass a second electron beam through the sample, the second electron beam having an initial energy level less than an initial energy level of the first electron beam. The imaging unit is configured to analyze the sample based on the first electron beam and the second electron beam.

Further exemplary embodiments include an electron microscopy assembly. The electron microscopy assembly includes a first electron beam source configured to generate a first electron beam to travel in a first direction to contact a surface region of the sample and to scatter from the surface region of the sample and travel in a second direction opposite the first direction. The electron microscopy assembly further includes an imaging unit configured to receive the first and second low-voltage electron beams to generate data corresponding to the sample.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Transmission electron microscopy of organic materials, including biological materials, is notoriously difficult due to radiation damage caused by high-energy electrons. In exemplary embodiments, a first low-voltage electron beam is provided to detect characteristics on a surface of a sample and a second low-voltage electron beam is provided to pass through the sample and detect characteristics inside the sample.

Figure 1:
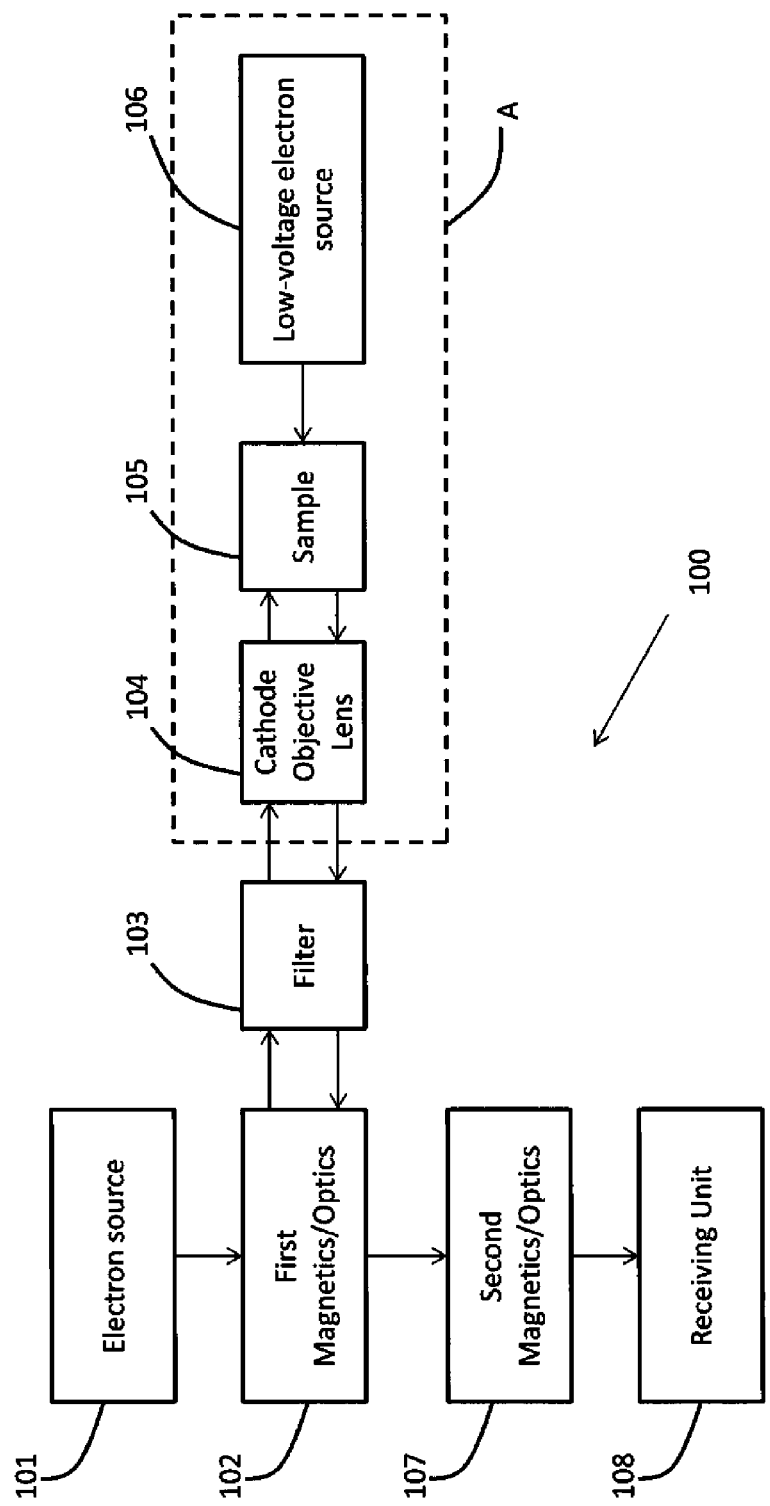
FIG. 1 illustrates a block diagram of an electron microscope assembly according to an embodiment of the present disclosure.

FIG. 1 illustrates a block diagram of an electron microscopy apparatus 100 according to an embodiment of the present disclosure. The apparatus 100 includes a first electron source 101 configured to provide a first electron beam, first magnetic deflection unit and optics 102 to modify characteristics of the first electron beam, a filter 103 to filter the first electron beam, a cathode objective lens 104 to focus the first electron beam, and a sample 105. The sample 105 may include a substrate having holes formed therein, and a material of interest may be provided in the holes. The sample is electrically biased relative to the objective lens so as to reduce the energy of the electrons beam generated by electron source 101, to an energy range of about 0 eV-100 eV. The system 100 is configured such that the electron source 101 emits the first electron beam at a high energy level, such as between 15 keV and 20 keV, and when the first electron beam reaches the sample 105, the electron beam has a low energy level, such as between about 0 eV and 100 eV. One or more of the first optics and magnetic deflector 102, the filter 103, the cathode objective lens 104, and a potential of the sample 105 may reduce an energy level of the first electron beam between the electron source 101 and the sample 105.

The magnetic deflector and optics 102 may include one or more of lenses, deflectors, and a magnet to focus and divide or redirect the first electron beam. The lenses may include, for example, a gun lens and a condenser lens. The magnet may be a prism array or an electron beam deflector configured to deflect the first electron beam from a first path from the electron source 101 to a second path toward the sample 105. In one embodiment, the magnet deflects the first electron beam by an angle of about ninety degrees (90°).

The filter 103 may include an aperture through which the first electron beam passes to cause only portions of the electron beam within predetermined height, length, radial dimensions, or energy to pass through to the sample 105. The cathode objective lens 104 may alter a magnification of an image generated by the electron beam and an energy level of the electron beam.

The sample 105 may be maintained at a potential similar to that of the electron source 101, such as between 15 kV and 20 kV. The first electron beam, or at least a portion of the first electron beam, may scatter at the surface of the sample 105 and reflect back to the cathode objective lens 104, filter 103 and first magnetics and/or optics 102. The surface of the sample may include an outer surface and a region just below the outer surface. The electron beam may pass through second magnetics and optics 107 and to a receiving unit 108 configured to receive the first electron beam, detect image patterns generated by the first electron beam, and output signals corresponding to the detected patterns. The receiving unit 108 may include an imaging unit to generate an image of the detected image patterns.

In one embodiment, the second magnetics and/or optics 107 includes one or more projection lenses. The second magnetics and/or optics 107 may also include one or more contrast apertures, mirror arrays, and magnets. For example, in one embodiment the electron beam exits the first magnetics and optics 102 in one direction and is diverted into another direction by a magnet or prism into a direction corresponding to an electron mirror or mirror array. The mirror or mirror array may be an electrostatic element. The first electron beam may be reflected from the mirror or mirror array back to the magnet or prism, and the magnet or prism may redirect the beam through one or more projection lenses toward the receiving unit 108.

The apparatus 100 further includes a low-voltage electron source 106 configured to generate a second electron beam having a low energy level, such as between around 0 eV (but not including 0 eV) and around 100 eV. For example, in one embodiment the low-voltage electron source 106 generates an electron beam having an energy level of about 5 eV. The second electron beam is of such an energy level that it passes through the sample 105 toward the first magnetics and optics 102. In other words, whereas the electron beam from the electron source 101 is deflected or scattered from a surface or surface region of the sample 105, obtaining surface information of the sample 105, the beam from the low-voltage electron source 106 passes through the sample 105. Both beams are directed by the first magnetics and optics 102 and the second magnetics and/or optics 107 to the receiving unit 108.

Both beams may be directed at the sample at the same time, or in one embodiment, either the first electron beam generated by source 101 or the second electron beam generated by source 106 is directed at the sample, while the other beam is not directed at the sample, or is turned off. In other words, data can be obtained with first electron beam alone, or with the second electron beam alone, or data can be obtained by both the first and second electron beams simultaneously.

In addition, embodiments of the present disclosure encompass a first electron beam having a portion scatter or reflect from the surface of the sample 105, while a portion is absorbed in or passes through the sample 105. The portion of the first beam that is scattered or reflected may be analyzed to analyze the sample 105, and the portion that is absorbed or passes through the sample 105 may not be analyzed. In addition, embodiments of the present disclosure encompass a second electron beam having a portion pass through the sample 105, while a portion is absorbed in or is scattered at a surface of the sample 105. The portion of the second beam that passes through the sample 105 may be analyzed to analyze the sample 105, and the portion that is absorbed or scattered by the sample 105 may not be analyzed Once the second electron beam from the low-voltage electron source 106 has passed through the sample 105, the energy level of the second electron beam may be increased to a high-voltage energy level. For example, in one embodiment, the energy level of the second electron beam is increased by one or more of the magnetics and optics 102, the filter 103, the cathode objective lens 104, and a voltage potential of the sample 105, to reach an energy level near the energy level of the first electron beam.

According to embodiments of the present disclosure, the apparatus 100 including first and second magnetics/optics 102 and 107 and the low-voltage electron source 106 may generate images of the sample 105 having a resolution of about 1 nm, and the second electron beam from the low-voltage electron source 106 does not damage the sample 105.

Although FIG. 1 illustrates an electron microscopy apparatus 100 having a particular configuration of magnetics and optics 102 and 107 and a receiving unit 108, embodiments of the present disclosure may be implemented in any electron microscopy apparatus capable of passing a low-voltage electron beam through a sample and generating data about the sample from the electron beam. Examples of electron microscopy apparatuses in which the low-voltage electron beam may be provided include a low-energy electron microscope (LEEM), Photo Electron Emission Microscope (PEEM), or any other suitable microscope.

Figure 2:
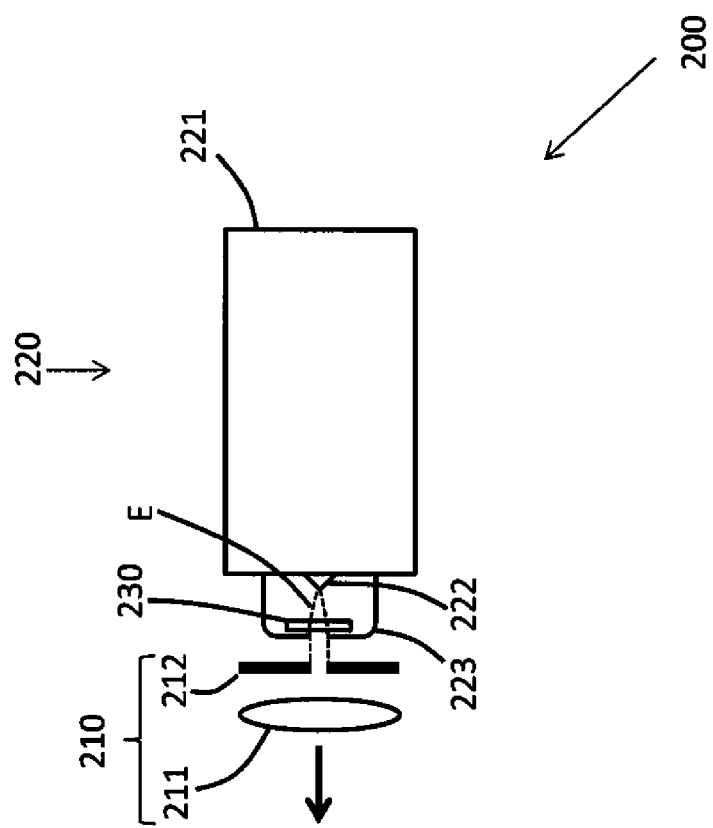
FIG. 2 illustrates a low-voltage electron beam portion of an electron beam microscope according to an embodiment of the present disclosure.

FIG. 2 illustrates a low-voltage electron source portion 200 according to embodiments of the present disclosure. The low-voltage electron source portion 200 corresponds to the region A of FIG. 1. The low-voltage electron source portion 200 includes an objective cathode lens 210 and an electron source assembly 220. The objective lens 210 includes a lens 211 including an entrance aperture 212. The objective lens 210 may decelerate an electron beam moving toward the sample 230 and may accelerate an electron beam moving from the sample 230 to the objective lens 210. In particular, the sample 230 may be maintained at a negative potential, while the entrance aperture 212 of the objective lens 210 facing the sample may be maintained at a ground potential. Accordingly, electrons leaving the sample 230 may be accelerated towards the objective lens 210. Alternatively the sample may be held at or near ground potential, while the objective lens 210 including the aperture 212 is held at a positive high potential, so that the electrons are accelerated towards the objective lens 210.

The electron beam assembly 220 includes a holder 221, which may be an electrically insulating holder, such as a ceramic holder. The electron beam assembly further includes an electron source 222 and a sample mount 223 onto which the sample 230 is mounted. As discussed above, in embodiments of the present disclosure, the electron source 222 is a low-voltage electron source configured to generate a low-voltage electron beam E having an energy level between about 0 eV (but not including 0 eV) and 100 eV. The electron beam E passes through the sample 230 and interacts with the sample 230 to generate patterns in the electron beam that may be detected by a receiving unit, such as the receiving unit 108 of FIG. 1, to obtain data about the sample 230 and/or generate an image corresponding to the sample 230.

Figure 3:
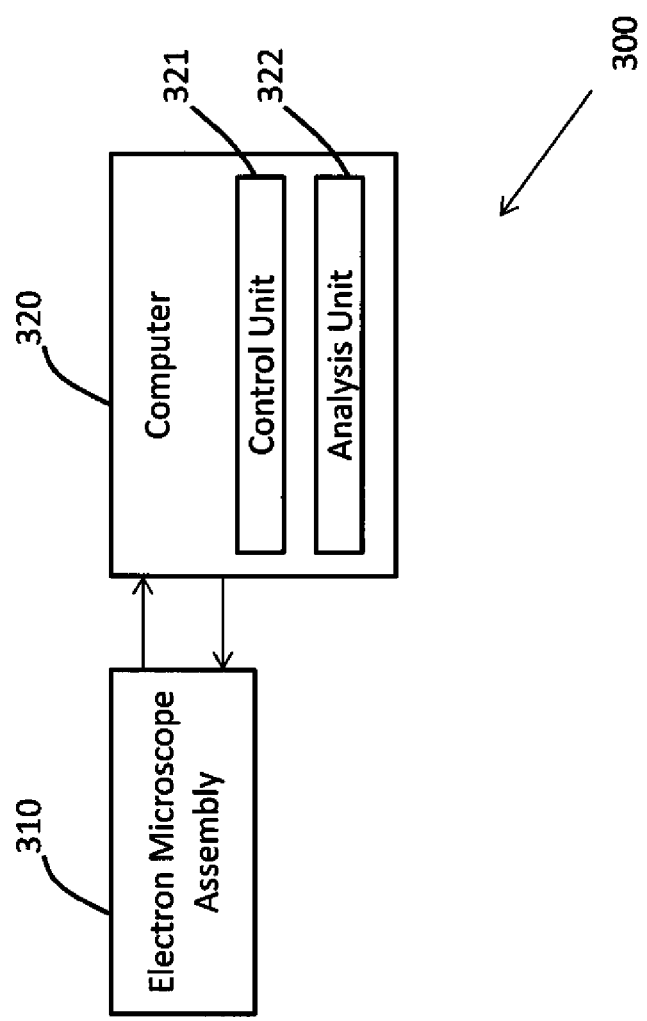
FIG. 3 is a block diagram of an electron volt microscope system according to an embodiment of the disclosure.

FIG. 3 illustrates a system 300 according to an embodiment of the present disclosure. The system includes an electron microscope assembly 310 in communication with a computer 320. For example, the electron microscope assembly may correspond to the electron microscopy apparatus 100 of FIG. 1. The computer 320 includes a control unit 321 and an analysis unit 322. The control unit 321 may include a processor, memory, logic, and other circuitry to control operation of the electron microscope assembly 310. For example, the control unit 321 may operate according to a program stored in memory and executed by a processor or according to manual user controls to control voltage levels of one or more electron beams, transmission times, transmission durations, lens positions, sample positions, receiving unit positions, or any other characteristic of the electron microscope assembly 310 for controlling operation of the electron microscope assembly 310.

The analysis unit 322 may receive data from the electron microscope assembly 310, such as from a receiving unit 108, as illustrated in FIG. 1, configured to detect patterns in one or more electron beams and transmit corresponding signals to the computer 320. The analysis unit 322 may include computer programs executed by a processor, as well as manual controls, to control analysis, storage, and display of the data from the receiving unit 108. The analysis unit 322 may include, for example, an imaging unit to generate an image of the sample based on the detected patterns in the electron beams.

Although FIG. 3 illustrates a block diagram of a system 300 according to embodiments of the present disclosure for purposes of description, it is understood that embodiments may include additional features not illustrated in FIG. 3, such as I/O hardware, wired communication interfaces, wireless communication interfaces, storage devices, display units, user interfaces, and other functional units.

Figure 4:
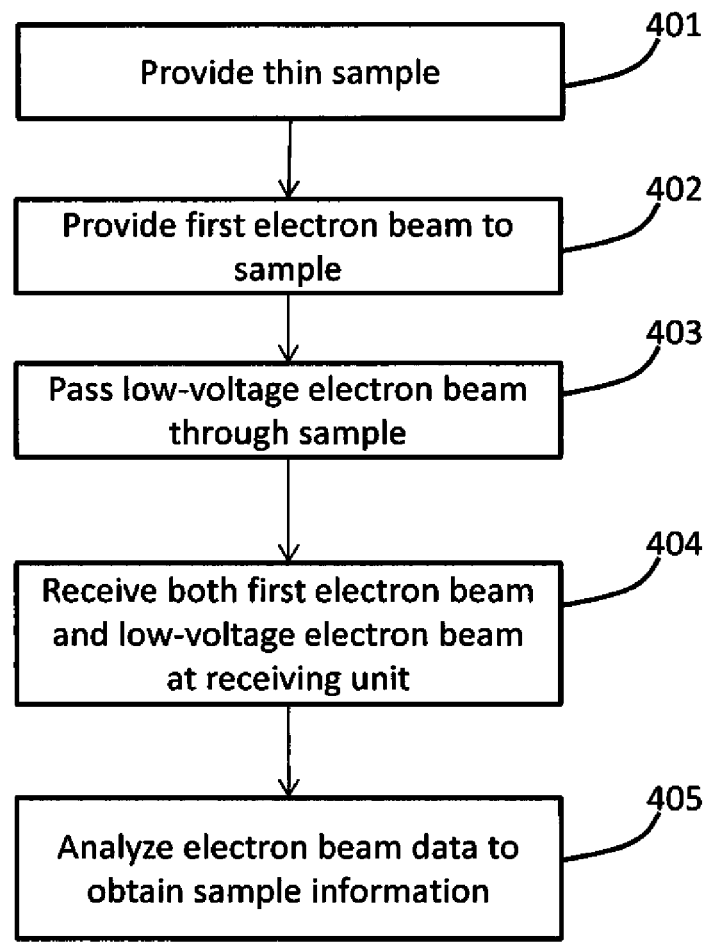
FIG. 4 is a flowchart illustrating a method according to one embodiment of the present disclosure.

FIG. 4 illustrates a method according to an embodiment of the present disclosure. In block 401, a sample is provided in an electron microscopy assembly. The sample may include a substrate having holes formed therein, and a material of interest may be provided in the holes. In block 402, a first electron beam is provided to the sample. In one embodiment, the first electron beam is controlled to have a voltage potential that is low relative to the voltage potential of the sample. For example, the first electron beam may have a potential between around 15 keV and 20 keV when emitted from an electron source and may have a potential reduced to between around 0 eV and 100 eV when the first electron beam reaches the sample. The first electron beam, or at least a portion of the first electron beam, may be reflected, deflected, or scattered at the surface of the sample, or at a surface region of the sample. Any portion of the first electron beam that passes through the sample may not be utilized for analysis of the sample.

In block 403, a low-voltage electron beam is provided to the sample and it passes through the sample, or at least a portion of the low-voltage electron beam passes through the sample. The low-voltage electron beam may have an energy level between about 0 eV and 100 eV and may be provided to the sample from a side opposite the first electron beam. Embodiments of the present disclosure encompass a low-voltage electron beam having a portion pass through the sample and a portion scatter upon contacting the sample. The portion that passes through the sample may be used for analysis of the sample, and the portion that scatters may be disregarded.

The low-voltage electron beam and/or the first electron beam may be received by a receiving unit in block 404. The receiving unit may be a device capable of detecting electron energy and generating signals based on the detected electron energy. When the first beam interacts with the surface of the sample, patterns may be generated in the first beam corresponding to characteristics of the surface region of the sample. Likewise, when the low-voltage beam passes through the sample, patterns may be generated in the low-voltage electron beam corresponding to characteristics in the sample. The receiving unit may be configured to detect the patterns in the first electron beam and the low-voltage electron beam, and my generate signals based on the detected patterns.

Although FIG. 4 describes a low-voltage electron beam being analyzed by the receiving unit, it is understood that the term "low-voltage electron beam" refers to the voltage at which the electron beam was generated and is used to distinguish the low-voltage electron beam from the first electron beam. Upon passing through the sample, the energy level of the low-voltage electron beam may be increased to a relatively higher voltage, such as a same voltage as the first electron beam.

In block 405, the signals may be analyzed to obtain sample information, such as images, composition data, physical features, or other information about the sample. Analyzing the signals may include generating an image based on the signals, and the image may include an image of the sample.

Figure 5:
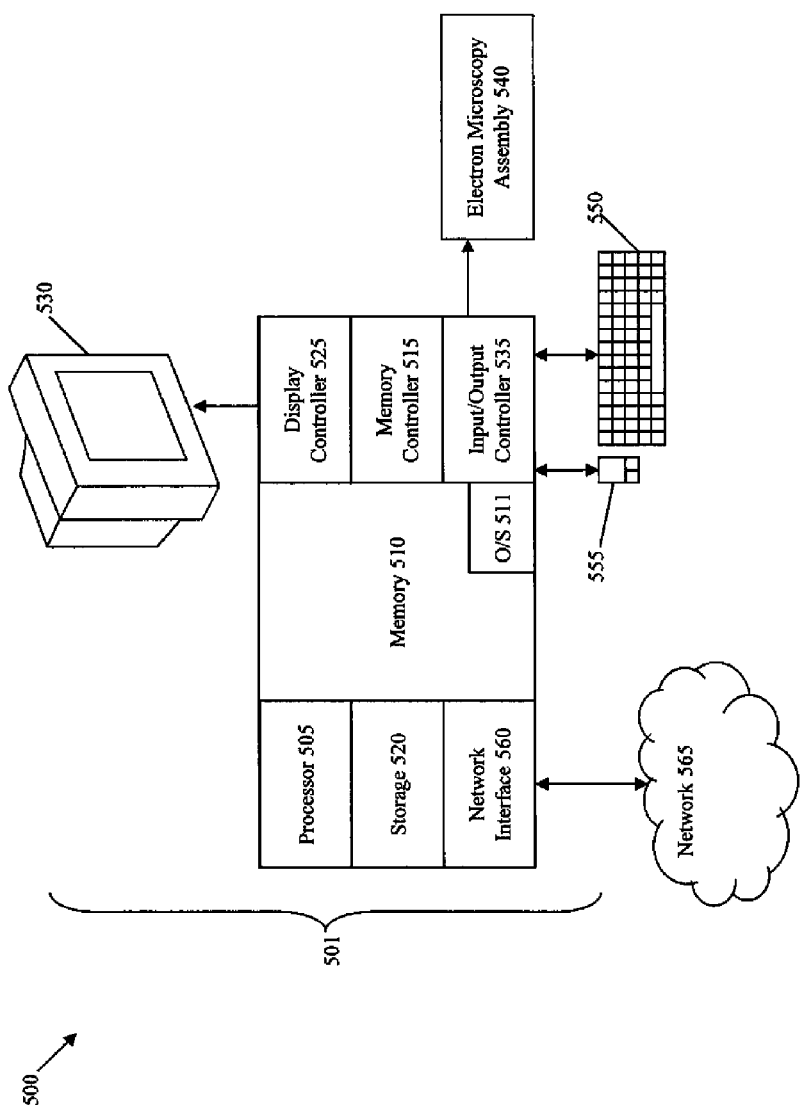
FIG. 5 illustrates a computer system according to an embodiment of the present disclosure.

FIG. 5 illustrates a block diagram of a system 500 for controlling and analyzing data of an electron microscopy assembly 540 according to embodiments of the present disclosure. The methods described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 500 therefore includes general-purpose computer 501 as illustrated in FIG. 5.

In an exemplary embodiment, in terms of hardware architecture, as shown in FIG. 5, the computer 501 includes a processor 505 including a plurality of execution units, an error detection unit, a dispatch rules adjustment unit, and an instruction dispatch unit. The computer 501 further includes memory 510 coupled to a memory controller 515, and an electron microscopy assembly 540 communicatively coupled via a local input/output controller 535. The input/output controller 535 can be, for example but not limited to, one or more buses or other wired or wireless connections, as is known in the art. The input/output controller 535 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 505 is a hardware device for executing software, particularly that stored in storage 520, such as cache storage, or memory 510. The processor 505 can be any custom made or commercially available processor, a central processing unit (CPU), an auxiliary processor among several processors associated with the computer 501, a semiconductor based microprocessor (in the form of a microchip or chip set), a macroprocessor, or generally any device for executing instructions.

The memory 510 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 510 may incorporate electronic, magnetic, optical, and/or other types of storage media.

Note that the memory 510 can have a distributed architecture, where various components are situated remote from one another, but can be accessed by the processor 505.

The instructions in memory 510 may include one or more separate programs, each of which comprises an ordered listing of executable instructions for implementing logical functions. In the example of FIG. 5, the instructions in the memory 510 a suitable operating system (OS) 511. The operating system 511 essentially controls the execution of other computer programs and provides scheduling, input-output control, file and data management, memory management, and communication control and related services.

In an exemplary embodiment, a conventional keyboard 550 and mouse 555 can be coupled to the input/output controller 535. The system 500 can further include a display controller 525 coupled to a display 530. In an exemplary embodiment, the system 500 can further include a network interface 560 for coupling to a network 565. The network 565 can be an IP-based network for communication between the computer 501 and any external server, client and the like via a broadband connection. The network 565 transmits and receives data between the computer 501 and external systems. In an exemplary embodiment, network 565 can be a managed IP network administered by a service provider. The network 565 may be implemented in a wireless fashion, e.g., using wireless protocols and technologies, such as WiFi, WiMax, etc. The network 565 can also be a packet-switched network such as a local area network, wide area network, metropolitan area network, Internet network, or other similar type of network environment. The network 565 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 501 is a PC, workstation, intelligent device or the like, the instructions in the memory 510 may further include a basic input output system (BIOS) (omitted for simplicity). The BIOS is a set of essential software routines that initialize and test hardware at startup, start the OS 511, and support the transfer of data among the hardware devices. The BIOS is stored in ROM so that the BIOS can be executed when the computer 501 is activated.

When the computer 501 is in operation, the processor 505 is configured to execute instructions stored within the memory 510, to communicate data to and from the memory 510, and to generally control operations of the computer 501 pursuant to the instructions.

In an exemplary embodiment, where execution unit error detection and dispatch rules adjustment is implemented in hardware, the dispatch rules adjustment methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 6:
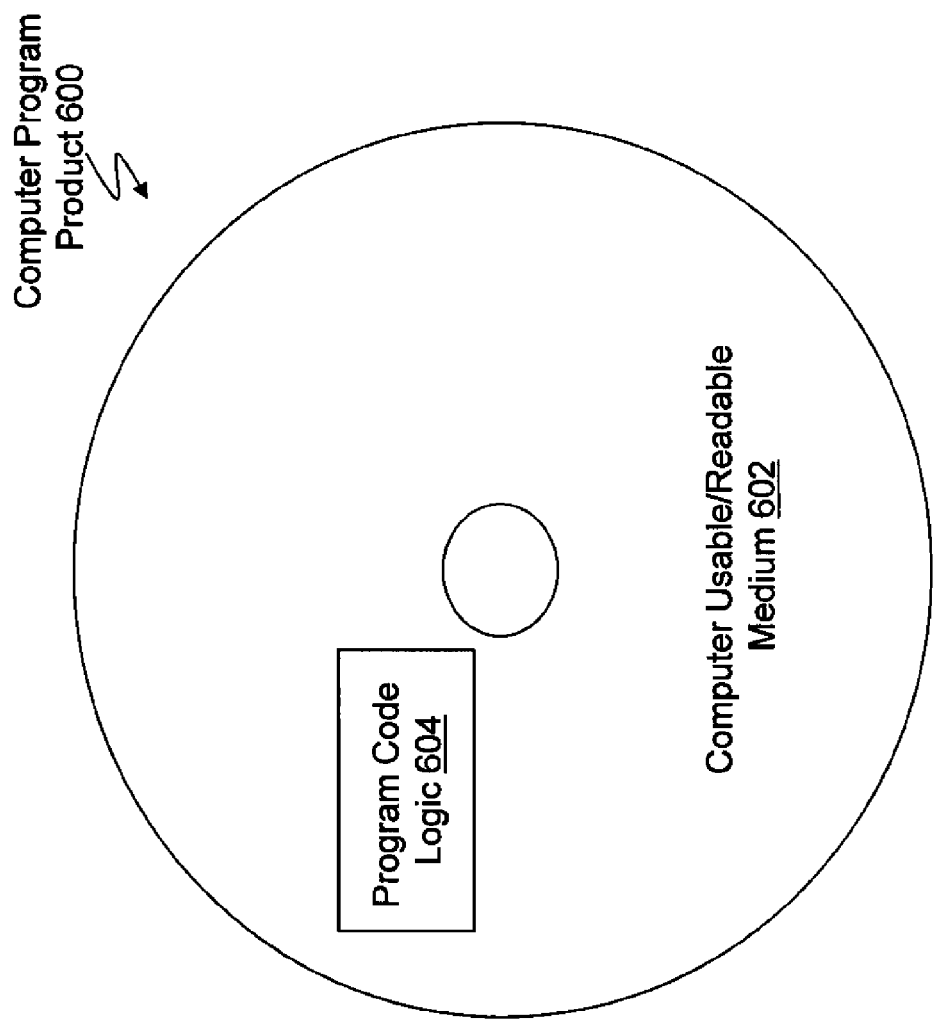
FIG. 6 illustrates a computer-readable medium according to an embodiment of the present disclosure.

As described above, embodiments for controlling and analyzing data from an electron microscopy assembly can be embodied in the form of computer-implemented processes and apparatuses for practicing those processes. An embodiment may include a computer program product 600 as depicted in FIG. 6 on a computer readable/usable medium 602 with computer program code logic 604 containing instructions embodied in tangible media as an article of manufacture. Exemplary articles of manufacture for computer readable/usable medium 602 may include floppy diskettes, CD-ROMs, hard drives, universal serial bus (USB) flash drives, or any other computer-readable storage medium, wherein, when the computer program code logic 604 is loaded into and executed by a computer, the computer becomes an apparatus for practicing the invention. Embodiments include computer program code logic 604, for example, whether stored in a storage medium, loaded into and/or executed by a computer, or transmitted over some transmission medium, such as over electrical wiring or cabling, through fiber optics, or via electromagnetic radiation, wherein, when the computer program code logic 604 is loaded into and executed by a computer, the computer becomes an apparatus for practicing the invention. When implemented on a general-purpose microprocessor, the computer program code logic 604 segments configure the microprocessor to create specific logic circuits.

In some embodiments, when the first and second electron beams have the same energy at the sample, the part of first beam that is reflected from the sample is complementary to the part of the second beam that passes through the sample. In addition, a part of the first and second electron beams may be absorbed by the sample, but when the first and second electron beams have the same electron energy at the sample, the absorbed parts will be the same for both beams.

In some embodiments, a total beam intensity of the first beam may be determined by setting the sample potential such that all electrons in the second electron beam are reflected, without the electrons from the first electron beam touching the sample. By a comparison of the intensities of the first and second electron beams arriving at the sample with identical electron energy, and with the intensity of the first electron beam when it is fully reflected, the reflected, transmitted, and absorbed parts of the electron beams at that energy can be determined.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatuses, systems and computer program products according to embodiments of the disclosure. It will be understood that blocks of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that some blocks of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method comprising:
   generating a first electron beam;
   directing the first electron beam to a surface region of a sample;
   generating a second electron beam;
   directing the second electron beam to the sample to pass through the sample, the second electron beam having an initial energy level less than an initial energy level of the first electron beam; and
   analyzing at least one of the first electron beam and the second electron beam to obtain information about the sample.

2. The method of claim 1, wherein the first electron beam is directed to the sample in a first direction and the second electron beam is directed to the sample in a second direction opposite the first direction.

3. The method of claim 1, further comprising:
reducing an energy level of the first electron beam approaching the sample; and
increasing an energy level of at least one of the first electron beam and the second electron beam moving away from the sample.

4. The method of claim 1, wherein the initial energy level of the second electron beam is at least one order of magnitude less than the initial energy level of the first electron beam.

5. The method of claim 1, wherein directing the first electron beam to the surface region of a sample includes reducing an energy level of the first electron beam approaching the sample to interact with the surface region of the sample.

6. The method of claim 1, wherein the first electron beam has an initial voltage in a range from about 10 keV to about 100 keV, and the second electron beam has an initial voltage in a range from about 0 eV to about 100 eV.

7. A method comprising:
directing a first electron beam to a surface region of sample in a first direction;
directing a second electron beam to the sample in a second direction to pass through the sample, the second direction being opposite the first direction and the second electron beam having an initial energy level less than an initial energy level of the first electron beam;
accelerating at least one of the first and second electron beams from the sample in the second direction; and
analyzing at least one of the first electron beam and the second electron beam to obtain information about the sample.

8. The method of claim 7, further comprising:
reducing an energy level of the first electron beam approaching the sample; and
increasing an energy level of both the first electron beam and the second electron beam moving away from the sample.

9. The method of claim 7, wherein the initial energy level of the second electron beam is at least one order of magnitude less than the initial energy level of the first electron beam.

10. The method of claim 7, wherein directing the first electron beam to the surface region of a sample includes reducing an energy level of the first electron beam approaching the sample to interact with the surface region of the sample.

11. The method of claim 7, wherein the first electron beam has an initial voltage in a range from about 10 keV to about 100 keV, and the second electron beam has an initial voltage in a range from about 1 eV to about 100 eV.

12. A method comprising:
directing a first electron beam to a surface region of sample;
directing a second electron beam to the sample to pass through the sample, the second electron beam having an initial energy level less than an initial energy level of the first electron beam; and
analyzing the first electron beam and the second electron beam to obtain information about the sample.

13. The method of claim 12, further comprising:
reducing an energy level of the first electron beam approaching the sample; and
increasing an energy level of both the first electron beam and the second electron beam moving away from the sample.

14. The method of claim 12, wherein the initial energy level of the second electron beam is at least one order of magnitude less than the initial energy level of the first electron beam.

15. The method of claim 12, wherein directing the first electron beam to the surface region of a sample includes reducing an energy level of the first electron beam approaching the sample to interact with the surface region of the sample.

16. The method of claim 12, wherein the first electron beam has an initial voltage in a range from about 10 keV to about 100 keV, and the second electron beam has an initial voltage in a range from about 1 eV to about 100 eV.

17. The method of claim 12, wherein the first electron beam is directed to the sample in a first direction and the second electron beam is directed to the sample in a second direction opposite the first direction.

18. The method of claim 17, wherein the first and second electron beams move away from the sample co-linearly in the second direction.

\* \* \* \* \*